US012065403B2

(12) United States Patent
Chakrabarti et al.

(10) Patent No.: US 12,065,403 B2
(45) Date of Patent: Aug. 20, 2024

(54) ACID CATALYZED SYNTHESIS OF METHYL ACRYLATE FROM ACRYLIC ACID AND METHANOL

(71) Applicant: Rohm and Haas Company, Collegeville, PA (US)

(72) Inventors: Reetam Chakrabarti, Phoenixville, PA (US); Minh N. Ngo, Philadelphia, PA (US); James Elder, Friendswood, TX (US)

(73) Assignee: Rohm and Haas Company, Collegeville, PA (US)

( * ) Notice: Subject to any disclaimer, the term of this patent is extended or adjusted under 35 U.S.C. 154(b) by 516 days.

(21) Appl. No.: 17/601,094

(22) PCT Filed: Apr. 2, 2020

(86) PCT No.: PCT/US2020/026282
§ 371 (c)(1),
(2) Date: Oct. 4, 2021

(87) PCT Pub. No.: WO2020/214422
PCT Pub. Date: Oct. 22, 2020

(65) Prior Publication Data
US 2022/0153679 A1     May 19, 2022

Related U.S. Application Data

(60) Provisional application No. 62/834,464, filed on Apr. 16, 2019.

(51) Int. Cl.
*C07C 67/08*     (2006.01)
*B01D 3/14*     (2006.01)
(Continued)

(52) U.S. Cl.
CPC .............. *C07C 67/08* (2013.01); *B01D 3/146* (2013.01); *B01D 3/40* (2013.01); *B01D 5/006* (2013.01);
(Continued)

(58) Field of Classification Search
CPC ......... C07C 67/08; C07C 67/54; C07C 67/58; C07C 69/54; B01D 3/146
See application file for complete search history.

(56) References Cited

U.S. PATENT DOCUMENTS 4,280,010 A     7/1981    Erpenbach et al.
5,945,560 A *   8/1999    Iffland .................... C07C 67/54
                                                                                                  560/205
(Continued)

OTHER PUBLICATIONS

Pendergast, "Consider Dividing Wall Columns," Chemical Processing, 2008.

*Primary Examiner* — Yate' K Cutliff
(74) *Attorney, Agent, or Firm* — Brian L. Mutschler

(57) ABSTRACT

A method for preparing methyl acrylate comprises heating in a reaction zone a mixture comprising acrylic acid, methanol, and an acid catalyst to react and form a reaction product comprising methyl acrylate which is vaporized with other light components and then fed to a distillation zone. A feed stream entering the reaction zone comprises methanol and acrylic acid in a molar ratio of greater than 1 and less than 2, and a residence time in the reaction zone ranges from 0.25 to 2 hours. A distillate from the distillation zone is condensed and phase-separated to form an organic phase comprising methyl acrylate and an aqueous phase. A portion of the organic phase is returned to the distillation zone as organic reflux. The remainder of the organic phase and the aqueous phase of the distillation zone is fed to an extraction column to form a methanol rich aqueous effluent and an organic effluent comprising methyl acrylate. The organic (Continued)

effluent from the extraction column is purified in a single finishing column, wherein a light ends stream is removed from the top of the finishing column, a bottoms stream is removed from the bottom of the finishing column, and methyl acrylate is removed from a side draw stream.

11 Claims, 2 Drawing Sheets

(51) Int. Cl.
*B01D 3/40* (2006.01)
*B01D 5/00* (2006.01)
*C07C 67/54* (2006.01)
*C07C 67/58* (2006.01)
*C07C 69/54* (2006.01)

(52) U.S. Cl.
CPC .............. *C07C 67/54* (2013.01); *C07C 67/58* (2013.01); *C07C 69/54* (2013.01)

(56) References Cited

U.S. PATENT DOCUMENTS

| | | | |
|---|---|---|---|
| 9,796,651 B2 | 10/2017 | Fauconet et al. | |
| 2004/0236143 A1* | 11/2004 | Martan | C07C 67/08 560/205 |

* cited by examiner

ACID CATALYZED SYNTHESIS OF METHYL ACRYLATE FROM ACRYLIC ACID AND METHANOL

FIELD OF THE INVENTION

The present invention relates to a process for the acid catalyzed synthesis of methyl acrylate from acrylic acid and methanol.

BACKGROUND OF THE INVENTION

Various processes for preparing (meth)acrylates from (meth)acrylic acid and alcohols using acid catalysts have been proposed.

U.S. Patent Application Publication No. 2004/0236143 discloses a process in which (meth)acrylates are prepared by reacting (meth)acrylic acid, which may be a crude (meth) acrylic acid, with an alcohol in the presence of at least one acid catalyst. In the process, acrylic acid is reacted in the presence of at least one acid catalyst with the alcohol in a reaction zone connected to a distillation unit. The (meth) acrylic acid, along with the low boilers, Michael adducts, and water of reaction are condensed and sent to a scrubbing unit to be treated with a wash liquid. The discharge from the wash step is separated into an organic phase and an aqueous phase, and some of the organic phase is passed as reflux in the distillation unit while the remainder is subjected to low boiler removal, where the organic phase from the distillate is subjected to a further distillation unit. The bottom product of the low boiler removal operation is subjected to purifying distillation to provide the desired ester.

The conventional processes for acid catalyzed synthesis of methyl acrylate are inefficient and require large quantities of wash liquid and energy. These processes also require multiple columns for purification of the product, which requires additional capital and further operating costs.

There is a need for more efficient processes that address one or more of these issues.

SUMMARY OF THE INVENTION

The present invention is directed to methods for preparing methyl acrylate.

According to one aspect of the present invention, a method for preparing methyl acrylate comprises:
  a) heating in a reaction zone a mixture comprising acrylic acid, methanol, and an acid catalyst to react and form a product comprising methyl acrylate which is vaporized with other light components and then fed to a distillation zone, wherein a feed stream entering the reaction zone comprises methanol and acrylic acid in a molar ratio of greater than 1 and less than 2, and a residence time in the reaction zone ranges from 0.25 to 2 hours;
  b) condensing and phase-separating a distillate from the distillation zone to form an organic phase comprising methyl acrylate and an aqueous phase;
  c) returning a portion of the organic phase to the distillation zone as organic reflux;
  d) feeding the remainder of the organic phase and the aqueous phase of the distillation zone to an extraction column to form a methanol rich aqueous effluent and an organic effluent comprising methyl acrylate; and
  e) purifying the organic effluent from the extraction column in a single finishing column, wherein a light ends stream is removed from the top of the finishing column, a bottoms stream is removed from the bottom of the finishing column, and methyl acrylate is removed from a side draw stream.

DETAILED DESCRIPTION OF EMBODIMENTS OF THE INVENTION

Figure 1:
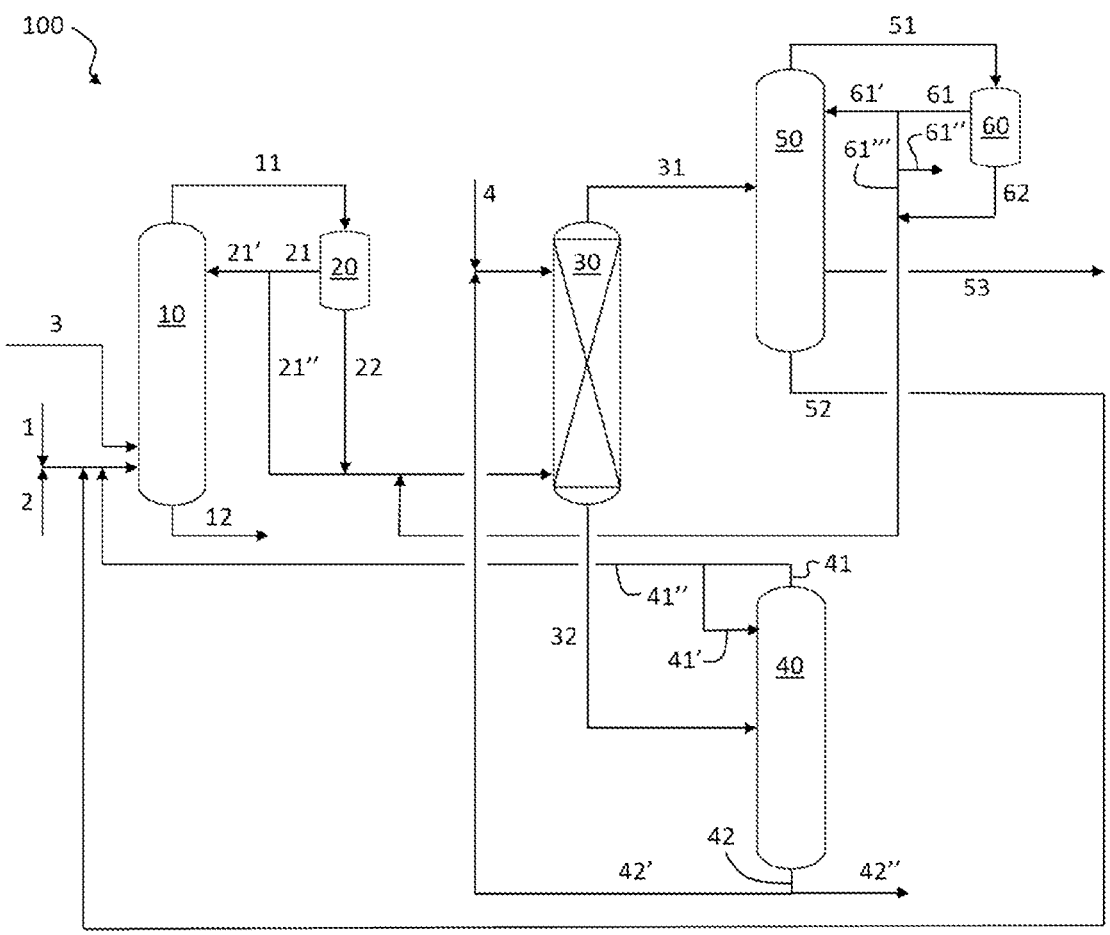
FIG. 1 shows a schematic representation according to an embodiment according to the present invention using a distillation column with a side draw as the finishing column.

As used herein, the terms "a," "an," "the," "at least one," and "one or more" are used interchangeably. The terms "comprises," "includes," "contains," and variations thereof do not have a limiting meaning where these terms appear in the description and claims. Thus, for example, a mixture that includes a polymerization inhibitor can be interpreted to mean that the mixture comprises at least one polymerization inhibitor.

As used herein, recitations of numerical ranges by endpoints includes all numbers subsumed in that range (e.g. 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.1 to 100, from 1 to 99.99, from 1.01 to 99.99, from 40 to 6, from 1 to 55, etc.

As used herein, the recitations of numerical ranges and/or numerical values, including such recitations in the claims, can be read to include the term "about." In such instances, the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety or its equivalent U.S. version is so incorporated by reference) especially with respect to the disclosure of definitions (to the extent not inconsistent with any definitions specifically provided in this disclosure) and general knowledge in the art.

One aspect of the present invention relates to a method for preparing methyl acrylate comprising heating in a reaction zone, a mixture comprising acrylic acid, methanol, and an acid catalyst to react and form a product comprising methyl acrylate. The reaction within the reaction zone occurs in the liquid phase.

In the inventive process, the feed stream to the reaction zone comprises a molar excess of methanol with respect to acrylic acid, i.e., the molar ratio of methanol to acrylic acid fed to the reaction zone is greater than 1. The molar ratio of methanol to acrylic acid is the molar ratio of the methanol to acrylic acid in the combined feed stream fed to the reaction zone, which may include both fresh feed entering into the system and recycle streams from other unit operations within the system. As used herein, the terms "combined feed stream" and "feed stream" means all of the reactants entering the reaction zone, including reactants entering the system (i.e., fresh feed) and reactants recycled from other unit operations in the system.

For example, the molar ratio of methanol to acrylic acid fed to the reaction zone may be greater than or equal to 1.05, 1.1, 1.2, 1.3, 1.4, 1.5, 1.6, 1.7, or 1.8. Preferably, the molar ratio of methanol to acrylic acid is greater than or equal to 1.1. More preferably, the molar ratio of methanol to acrylic acid is greater than or equal to 1.2. Even more preferably, the molar ratio of methanol to acrylic acid is greater than or equal to 1.3.

The molar ratio of methanol to acrylic acid may be less than or equal to 2. For example, the molar ratio of methanol to acrylic acid may be less than or equal to 1.9, 1.8, 1.7, 1.6, or 1.5. Preferably, the molar ratio of methanol to acrylic acid is less than or equal to 1.8. More preferably, the molar ratio of methanol to acrylic acid is less than or equal to 1.7. Even more preferably, the molar ratio of methanol to acrylic acid is less than or equal to 1.6.

The molar ratio may be a range between any of endpoints disclosed above. For example, the molar ratio may range from 1.1 to 1.8, from 1.2 to 1.9, from 1.3 to 1.6, etc. Preferably, the molar ratio of the methanol to acrylic acid fed to the reaction zone ranges from 1.1 to 1.8. More preferably, the molar ratio of methanol to acrylic acid ranges from 1.2 to 1.7. Even more preferably, the molar ratio of methanol to acrylic acid ranges from 1.3 to 1.6.

The acrylic acid introduced into the process is preferably an overhead grade of acrylic acid, which has been distilled to remove heavy ends components such as dimer (e.g., Michael adducts) and maleic acid. The acrylic acid fed to the system may comprise at least 98 wt. % acrylic acid, such as, for example, at least 98.5 wt. % acrylic acid or at least 99 wt. % acrylic acid. Preferably, the acrylic acid is substantially free of impurities, such as Michael adducts and acetic acid. As used herein, the term "substantially free of impurities" means that the acrylic acid contains less than 2 wt. % of impurities, preferably less than 1.5 wt. % of impurities, and more preferably, less than 1 wt. % of impurities.

The mixture introduced into the system (i.e., the fresh feed stream) may comprise, consist essentially of, or consist of acrylic acid, methanol, acid catalyst, and, optionally, a polymerization inhibitor. As used herein, "consist essentially of acrylic acid, methanol, and acid catalyst" means that the fresh feed stream does not include any impurities that will foul the system or adversely affect the yield of methyl acrylate. As used herein, the term "fresh feed stream" means the material entering into the system and excludes any materials that are recycled within the system. Preferably, the fresh feed stream is fed continuously to the system such that the process is a continuous process.

If a lower grade acrylic acid is used, the acrylic acid may be purified by any known process prior to being fed to the reaction zone.

Polymerization inhibitors may include alkylphenols, e.g. o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol or 2,2'-methylenebis(6-tert-butyl-4-methyphenol); hydroxyphenols, e.g. hydroquinone, 2-methylhydroquinone, 2,5-di-tert-butylhydroquinone, pyrocatechol (1,2-dihydroxybenzene) or benzoquinone; aminophenols, e.g. para-aminophenol; nitrosophenols, e.g. para-nitrosophenol; alkoxyphenols, e.g. 2-methoxyphenol (guajacol, pyrocatechol monomethyl ether), 2-ethoxyphenol, 2-isopropxyphenol, 4-methoxyphenol (hydroquinone monomethyl ether), mono- or di-tert-butyl-4-methoxyphenol; tocopherols, e.g. α-tocopherol, and 2,3-dihydro-2,2-dimethyl-7-hydroxybenzofuran (2,2-dimethyl-7-hydroxycoumarane); N-oxyls, e.g., 4-hydroxy-2,2,6,6-tetramethylpiperidin-N-oxyl, 4-oxo-2,2,6,6-tetramethylpiperidin-N-oxyl, 4-acetoxy-2,2,6,-6-tetramethylpiperidin-N-oxyl, 2,2,6,6-tetramethylpiperidin-N-oxyl, 4,4',4"-tris(2,2,6,6-tetramethylpiperidin-N-oxyl) phosphite or 3-oxo-2,2,5,5-tetramethylpyrrolidin-N-oxyl; aromatic amines or phenylenediamines, e.g. N,N-diphenylamine, N-nitrosodiphenylamine, N,N'-dialkyl-para-phenylenediamine; hydroxylamines, e.g. N,N-diethylhydroxylamine; phosphorus-containing compounds, e.g. triphenylphosphine, triphenyl phosphite, hypophosphorous acid or triethyl phosphite; sulfur-containing compounds, e.g. diphenyl sulfide or phenothiazine. When included in the feed stream, the polymerization inhibitor may be present in an amount ranging from 0.01 to 0.1 wt. %. Additional polymerization inhibitor may be added elsewhere in the system as desired.

The acid catalyst may comprise sulfuric acid or a sulfonic acid, such as, for example, p-toluenesulfonic acid (PTSA), benzenesulfonic acid, dodecylbenzenesulfonic acid, methanesulfonic acid (MSA), and mixtures thereof. Preferably, the acid catalyst is sulfuric acid.

The acid catalyst may be present in an amount ranging from 1 to 10 wt. % based on the total weight of the liquid bleed, i.e., the bottoms stream exiting the reaction zone. Preferably, the acid catalyst is present in an amount ranging from 2 to 8 wt. % relative to the total weight of the bottoms stream exiting the reaction zone. More preferably, the acid catalyst is present in an amount ranging from 3 to 7 wt. % relative to the total weight of the bottoms stream exiting the reaction zone.

The reaction zone has a volume that provides the feed stream with a residence time of at least 0.25 hours. For example, the volume of the reaction zone provides the feed stream with a residence time of at least 0.35 hours or at least 0.5 hours. Preferably, the residence time of the reaction zone is at most 2.5 hours, such as, at most 2 hours, at most 1.5 hours, or at most 1 hour.

The products may exit the reaction zone as either a vapor, which enters the distillation zone, or as the liquid bleed. The liquid bleed can be disposed of as organic waste. The liquid bleed may comprise less than 5 wt. % based on the total amount of reactants entering the system, i.e., the combined feed stream.

The temperature within the reaction zone may range from 60 to 160° C., preferably from 70 to 150° C., more preferably from 90 to 140° C., and even more preferably from 100 to 130° C. The column may be operated at atmospheric pressure. Therefore, the reaction zone may be operated at slightly above atmospheric pressure, such as, for example, 0.1 to 5 psig.

As used herein, the term "reaction zone" refers to where the reaction of the acrylic acid with methanol takes place in the presence of an acid catalyst. The reaction zone may comprise, for example, a reactor, such as a glass-lined vessel, having a reboiler to provide heating to reaction temperature and boil-up for product/lights removal or separation from the catalyst, or the bottom stage of a distillation column. Preferably, the reaction zone comprises a reactor that acts as a sump to a distillation column.

As used herein, the term "distillation zone" refers to an area in a distillation column in which the separation of components takes place. The distillation zone may comprise a distillation column connected to a reactor (i.e., the reaction zone). When the reaction zone comprises the bottom stage of a distillation column, the distillation zone may comprise the other stages of the distillation column. Preferably, the distillation zone comprises a distillation column, which is connected to a separate reactor comprising the reaction zone, and functions as the column's bottom stage.

The distillate from distillation zone may be condensed by any conventional means, such as, for example a shell and tube condenser, to form a condensate comprising a 2-phase distillate product. The condensate may be phase-separated to form an organic phase and an aqueous phase. The phase-separation may be performed in any liquid-liquid separator known in the art, such as, for example, a decanter. The organic phase comprises primarily organic components including methyl acrylate. The aqueous phase comprises water formed in the reaction zone, as well as soluble fractions of organic materials, which include methanol and methyl acrylate.

A portion of the organic phase may be returned to the distillation zone as organic reflux. The portion of the organic phase returned to the distillation zone may comprise up to 67 wt. % of the total amount of the organic phase from the phase separator. Preferably, the portion of the organic phase returned to the distillation zone as reflux comprises at least 5 wt. % of the total amount of the organic phase from the phase separator, such as, at least 10 wt. %, at least 15 wt. %, at least 20 wt. %, at least 25 wt. %, at least 30 wt. %, or at least 40 wt. % of the total amount of the organic phase from the phase separator. Preferably, the portion of the organic phase returned to the distillation zone comprises less than 67 wt. %, less than 60 wt. %, less than 55 wt. %, or less than 50 wt. % of the total amount of the organic phase from the phase separator. Increasing the amount of the portion of organic phase returned to the distillation zone as reflux may increase the purity of the methyl acrylate product leaving the distillation zone but may also increase the equipment size and energy required.

The remainder of the organic phase, i.e., the organic phase not returned to the distillation zone as reflux, may be fed to an extraction column. The aqueous phase may be combined with the remainder of the organic phase and fed to the extraction column.

In the extraction column water is used to perform bulk separation of the excess methanol from the organic phase. The extraction column provides a methanol rich aqueous effluent and an organic effluent comprising primarily methyl acrylate. The methanol rich aqueous effluent also comprises soluble methyl acrylate.

The methanol rich aqueous effluent may then be fed to an alcohol recovery column. The alcohol recovery column may comprise a distillation column in which the methanol rich aqueous effluent is distilled to separate the water from the methanol and other organic components more volatile than water. The bottoms stream comprises water and is substantially free of organics more volatile than water.

As used herein, the term "substantially free of organics more volatile than water" refers to a bottoms stream that comprises less than 2 wt. % of organics more volatile than water based on the total weight of the bottoms stream, preferably less than 1 wt. % of organics more volatile than water, and more preferably less than 0.5 wt. % of organics more volatile than water. Preferably the bottoms stream is substantially comprised of water. As used herein, the term "substantially comprised of water" means that the bottoms stream comprises at least 97 wt. % water based on the total amount of the bottoms stream, preferably at least 98 wt. % water, more preferably at least 99 wt. % water, and even more preferably at least 99.5 wt. % water.

The distillate from the alcohol recovery column comprises methanol and organic components more volatile than water, including methyl acrylate. The distillate from the alcohol recovery column may be totally or partially condensed, and a portion of the condensed distillate may be returned to the alcohol recovery column as reflux. This reflux may comprise, for example, at least 65 wt. % of the total weight of the condensed distillate. Preferably, the portion of the condensed distillate fed to the alcohol recovery column as reflux may comprise at least 75 wt. % of the total weight of the condensed distillate, more preferably, at least 85 wt. %. The remainder of the distillate from the alcohol recovery column may be recycled to the reaction zone.

The bottoms stream from the alcohol recovery column may be disposed of as waste. Alternatively, a portion of the bottoms stream from the alcohol recovery column may be recycled and fed to the extraction column with the water used for the bulk separation of the excess alcohol from the organic phase. Preferably, a portion of the bottoms stream is recycled.

The organic effluent from the extraction column may be fed to a single finishing column for purification of the methyl acrylate. Preferably, no further purification steps are necessary. From the finishing column, a distillate composed of a light ends stream comprising organics more volatile than methyl acrylate is removed from the top of the finishing column, a bottoms stream comprising components less volatile than methyl acrylate is removed from the bottom of the finishing column, and methyl acrylate in a side draw stream from the middle portion of the finishing column. As used herein, the term "middle portion of the finishing column" means any position between the bottom and the top of the finishing column.

Preferably, less than 15 wt. % of the total amount of the feed entering the finishing column is removed in the light ends stream. More preferably, less than 13 wt. % of the total amount of the feed entering the finishing column is removed as light ends in the distillate. Even more preferably, less than 11 wt. % of the total amount of the feed entering the finishing column is removed as light ends in the distillate.

The light ends stream from the finishing column may be partially condensed and the condensed liquid separated into an organic phase and an aqueous phase. Some light impurities are not condensed and may be allowed to leave the process as vapors via a condenser vent system. A portion of the organic phase may be returned to the finishing column as organic reflux. For example, the portion of the organic phase returned to the finishing column as reflux comprises at least 50 wt. % of the total amount of the organic phase from the phase separator, such as, at least 60 wt. %, preferably at least 70 wt. %, more preferably at least 80 wt. %, and even more preferably at least 90 wt. % of the total amount of the organic phase from the phase separator.

Occasionally, a small fraction of the organic phase from the finishing column is bled from the system to facilitate light ends removal that has built up in the process.

The remainder of the organic phase from the light ends stream from the finishing column may be recycled to the extraction column. Likewise, the aqueous phase from the light ends stream may be recycled to the extraction column to be combined with the feed to the extraction column along with the remainder of the organic phase from the light ends stream.

The bottoms stream from the finishing column may be recycled to the reaction zone to recover additional methyl acrylate that may have exited the finishing column in the bottoms stream. Preferably, the bottoms stream from the finishing column comprises less than 40 wt. % of the total amount of the feed to the finishing column. More preferably, the bottoms stream from the finishing column comprises less than 30 wt. % of the total amount of the feed to the finishing column, and even more preferably comprises less than 20 wt. % of the total amount of the feed to the finishing column.

The methyl acrylate is removed from the finishing column in a side draw stream. The side draw stream may comprise at least 98 wt. % methyl acrylate relative to the total weight of the side draw stream. Preferably, the side draw stream comprises at least 99 wt. % methyl acrylate, and more preferably, at least 99.5 wt. % methyl acrylate.

The finishing column may comprise a distillation column with a side draw, or the finishing column may comprise a distillation column comprising a dividing wall which vertically bisects a portion of the interior of the distillation column to create a dividing section, i.e., a dividing wall distillation column. Dividing wall columns are known in the industry and their designs are discussed, for example, by Pendergast et al., "Consider Dividing Wall Columns," Chemical Processing (Dec. 19, 2008), which is hereby incorporated by reference.

In the dividing wall distillation column, the dividing wall does not extend to the top or bottom sections of the column, thus enabling the column to be refluxed and reboiled in the same way as a conventional column. The dividing wall separates the column into two sides to provide a fluid impermeable baffle separating the interior of the column. The feed inlet to the column is located on one side of the dividing wall while a side draw is located on the opposing side. The dividing wall enables the side of the column that does not have the inlet to function in a more stable manner with minimal effect from fluctuations in inlet flow rates, conditions or composition. This increased stability enables the column to be designed and operated in a manner that allows the side draw stream having a different composition from either the overhead stream or the bottoms stream to be removed from the column.

One embodiment of a process according to the present invention is shown schematically in FIG. 1. The system 100 has a reactor column 10 which is fed by a fresh feed of acrylic acid 1, methanol 2, and an acid catalyst 3. The fresh feed enters the bottom stage of reactor column 10, which is heated and acts as the reactive zone. A liquid bleed 12 exits the bottom stage of the reactor column 10. The upper stages of the reactor column 10 act as a distillation zone to rectify the reaction products, and the distillate 11 exits the top of the reactor column 10.

The distillate 11 from the reactor column 10 is condensed and then separated into an organic phase 21 and an aqueous phase 22 in decanter 20. A portion 21' of the organic phase 21 is returned to reactor column 10 as reflux, and the remainder 21" of the organic phase 21 is combined with the aqueous phase 22 and fed to an extraction column 30.

Fresh water feed 4 enters the top of the extraction column 30 and is used for bulk separation of excess methanol. A methanol rich aqueous effluent 32 exits the bottom of the extraction column 30, and an organic effluent 31 exits the top of the extraction column 30.

The methanol rich aqueous effluent 32 is fed to an alcohol recovery column 40, where a distillate 41 exits the top of the alcohol recovery column 40. A portion 41' of the distillate 41 is returned to the column as reflux and the remainder 41" of the distillate 41 is recycled back to the reactor column 10 to join the feed stream. A portion 42' of the bottoms stream 42 of the alcohol recovery column 40 is recycled to the top of extraction column 30 to join fresh water feed 4, and the remainder 42" of bottoms stream 42 is sent to waste.

The organic effluent 31 from extraction column 30 is fed to finishing column 50. In the embodiment shown in FIG. 1, finishing column 50 is a distillation column with a side draw. The light ends 51 of finishing column 50 are condensed and then separated into an organic phase 61 and an aqueous phase 62 in decanter 60. A portion 61' of organic phase 61 exiting decanter 60 is returned to the finishing column 50 as reflux, another portion 61" of organic phase 61 is bled from the system, and the remainder 61' of the organic phase 61 is combined with the aqueous phase 62 to be recycled back to the extractor column 30 to enter with the reactor column distillate 21" and 22 feed to the extractor column 30.

The bottoms stream 52 of the finishing column 50 is recycled to the reactor column 10.

Methyl acrylate is removed from the finishing column in side draw stream 53.

In FIG. 1, the combined feed to the reactor column 10 is comprised of the fresh feed (i.e., acrylic acid 1, methanol 2, and acid catalyst 3), as well as the distillate 41 from the alcohol recovery column 40 and the bottoms stream 52 from the finishing column 50.

Figure 2:
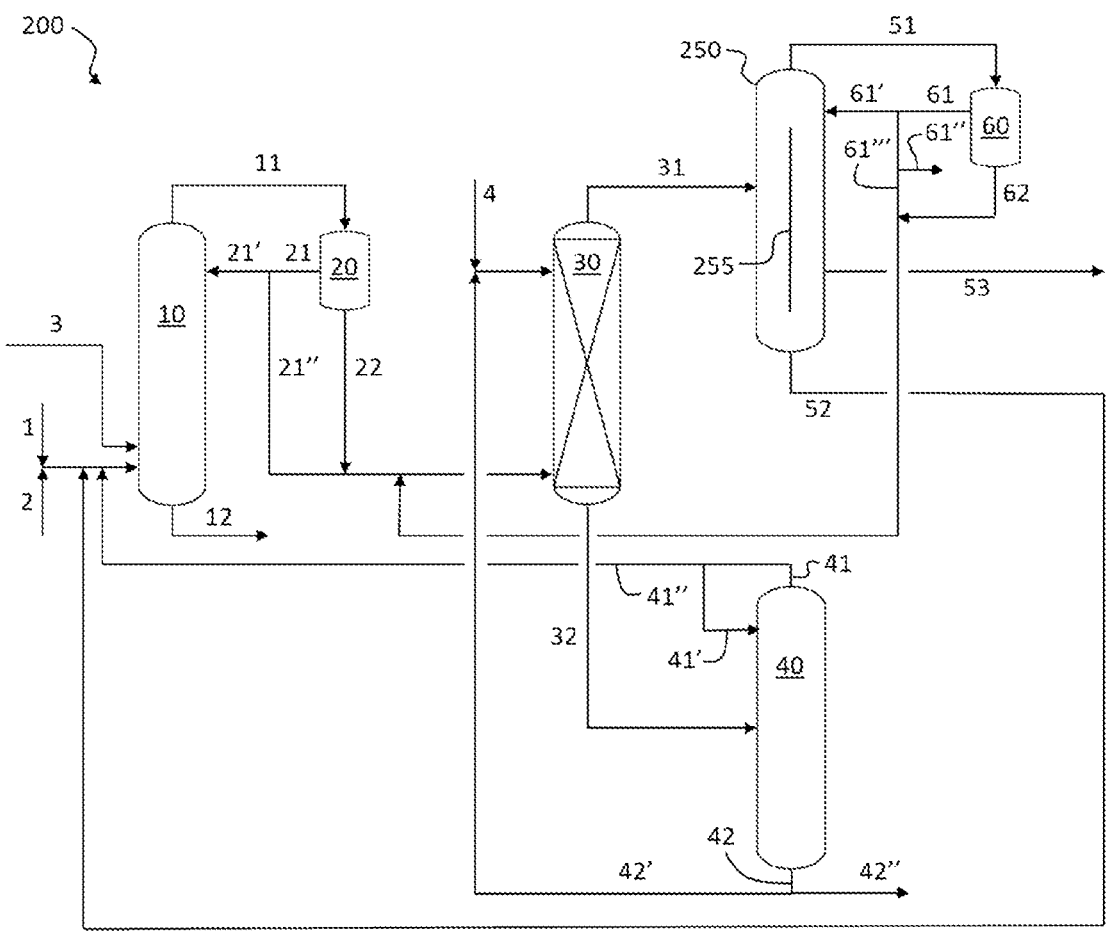
FIG. 2 shows a schematic representation according to an embodiment according to the present invention using a dividing wall column as the finishing column.

Another embodiment of a process according to the present invention is shown schematically in FIG. 2, in which similar elements are labeled with the same numbers as in FIG. 1. In FIG. 2, the system 200 finishing column 250 is a dividing wall finishing column. Finishing column 250 has a vertical wall 255 that divides the interior of the column into two sides. The organic effluent 31 from extraction column 30 enters the finishing column 250 on one side of the dividing wall 255. On the other side of the finishing column 250 opposite the inlet, a side draw is positioned to remove side draw stream 53.

The dividing wall 255 does not extend to the top or to the bottom of the finishing column 250. Preferably, the dividing wall 255 is sized such that substantially no heavy components that would desirably exit the bottoms stream 52 are present above the top of the dividing wall 255, and substantially no light components that would desirably exit the light ends 51 are present below the bottom of the dividing wall 255.

Example

The following example illustrates the present invention but is not intended to limit the scope of the invention.

In the present modeling example, a feed mixture is fed at a rate of 1044 g/h to the bottom stage of a distillation column with a working sump volume of 550 ml and 14 trays for rectification. The bottom stage has an efficiency of 100% while the 14 rectification trays have an efficiency of 50%. The feed mixture is made with a grade of acrylic acid that has been distilled to remove heavy end components, including dimer (e.g., Michael adducts) and maleic acid, and contains 0.05 wt. % of phenothiazine for inhibition. The feed mixture is modeled with a bulk composition is 46 wt. % acrylic acid, 31 wt. % methanol, 21 wt. % methyl acrylate, 0.7 wt. % water and 1 wt. % acrylic acid dimer, which results in a molar ratio of methanol to acrylic acid of 1.5. 98 wt. % sulfuric acid is added to the column bottom stage as needed to maintain the composition in the bottom stage at 5 wt. % sulfuric acid. Also, approximately 3 g/h of inhibitor solution is added to the condenser, which is composed of 6.2 wt. % phenothiazine and 6.2 wt. % hydroquinone in methyl acrylate. Additionally, 1 g/h of inhibitor solution is added to the reflux return line to the column, which is composed of 6 wt. % phenothiazine in methyl acrylate.

The reactor column bottoms stage is heated to maintain a temperature of 115° C., and the vapor product is fed to the distillation column operating at atmospheric pressure above the top tray, while the column bottom stage is operated at slightly above atmospheric pressure (0.2 psig) due to the pressure drop in the distillation column. A 48 g/h liquid bleed consisting primarily of heavies is drawn from the bottom stage.

The reaction products are rectified as they pass through the distillation column and the overhead vapors are condensed to produce a two-phase distillate product, which are separated into an organic phase and an aqueous phase. The organic phase consists of mostly methyl acrylate with 5.1 wt. % water, 8.4 wt. % methanol, and 0.3 wt. % methyl acetate. The aqueous phase is water with 27.8 wt. % methanol and 19.1 wt. % methyl acrylate. About 44 wt. % of the condensed organic phase is returned to the distillation column as reflux, and the remainder of the organic phase and the aqueous phase are sent to an extraction column.

The extraction step is performed at atmospheric conditions in a column with 6 stages. Water is fed at a rate of 811 g/h to the top of the column to perform the bulk separation of the excess methanol from the organic phase, which is fed to the bottom of the extractor column. 5 wt. % water in HQ is added to the column at a rate of 0.8 g/h. A methanol rich aqueous effluent containing water, 8.5 wt. % methyl acrylate, and 9.7 wt. % methanol is collected at a rate of 1153 g/h from the bottom of the column to be fed to an alcohol recovery column to recover the methyl acrylate and excess methanol. The organic effluent from the extractor consisting of primarily methyl acrylate with 2.7 wt. % water and 0.5 wt. % methyl acetate is collected at a rate of 717 g/h from the top of the extractor column to be fed to the light ends removal column.

The aqueous effluent from the extractor is fed to an alcohol recovery column with 36 trays for rectification. The condenser is fed 5 wt. % hydroquinone in methyl acrylate at 8 g/h. The alcohol recovery column is operated with a distillate to feed ratio of 0.19 and about 89% of the distillate is returned to the column as reflux. The distillate average bulk composition is 49 wt. % methanol, 46 wt. % methyl acrylate, 3.3 wt. % water, and is recycled back to the reactor as feed. The bottoms stream of the alcohol recovery column is composed of water with small quantities of other trace components.

An extractor organic effluent stream is sent to a finishing distillation column with 32 trays, a feed on tray 12 and run at a top pressure of 600 mmHg absolute, to remove light ends, which include methanol and methyl acetate. Also, approximately 3 g/h of inhibitor solution is added to the condenser, which is composed of 6.2 wt. % phenothiazine and 6.2 wt. % hydroquinone in methyl acrylate. Additionally, 1 g/h of inhibitor solution is added to the reflux line to the column, which is composed of 6.2 wt. % phenothiazine in methyl acrylate. The finishing column is operated so that the distillate is condensed to produce a two-phase distillate product, which is separated into an organic phase and an aqueous phase, and a portion of the organic phase is recycled back to the column. The finishing column is operated so that about 96% of the organic distillate is returned to the column as reflux, and the remainder of the organic distillate, 39 g/h, is combined with the aqueous distillate, 20 g/h, and both are recycled back to the extractor feed. A side draw stream containing 99.8 wt. % methyl acrylate is removed from tray 20 at 535 g/h, condensed and 5 g/h of 0.1 wt. % MeHQ in MA is added to the condensed stream. The bottoms stream is recycled back to the reactor to recover methyl acrylate and to permit any heavy components to leave in the liquid reactor bleed.

We claim:

1. A method for preparing methyl acrylate, comprising:
   a) heating in a reaction zone a mixture comprising acrylic acid, methanol, and an acid catalyst to react and form a product comprising methyl acrylate, which is vaporized with other light components and then fed to a distillation zone, wherein a feed stream entering the reaction zone comprises methanol and acrylic acid in a molar ratio of greater than 1 and less than 2, and a residence time in the reaction zone ranges from 0.25 to 2 hours;
   b) condensing and phase-separating a distillate from the distillation zone to form an organic phase comprising methyl acrylate and an aqueous phase;
   c) returning a portion of the organic phase to the distillation zone as organic reflux;
   d) feeding the remainder of the organic phase and the aqueous phase of the distillation zone to an extraction column to form a methanol rich aqueous effluent and an organic effluent comprising methyl acrylate; and
   e) purifying the organic effluent from the extraction column in a single finishing column, wherein a light ends stream is removed from the top of the finishing column, a bottoms stream is removed from the bottom of the finishing column, and methyl acrylate is removed from a side draw stream.

2. The method according to claim 1, wherein the acid catalyst is sulfuric acid or a sulfonic acid.

3. The method according to claim 1, wherein acrylic acid entering the reaction zone as fresh feed comprises less than 2 wt. % impurities.

4. The method according to claim 1, further comprising feeding the methanol rich aqueous effluent from the extraction column to an alcohol recovery column to form a distillate comprising methanol and a bottoms stream substantially free of organics more volatile than water.

5. The method according to claim 4, wherein at least a portion of the distillate of the alcohol recovery column is recycled to a reactive zone.

6. The method according to claim 4, wherein a portion of the bottoms stream of the alcohol recovery column is recycled to the extraction column.

7. The method according to claim 1, wherein the finishing column is a distillation column with a side draw.

8. The method according to claim 1, wherein the distillation column further comprises a dividing wall, wherein the organic effluent enters the dividing wall distillation column in a divided section on an opposing side of the dividing wall from the side draw.

9. The method according to claim 1, wherein the bottoms stream from the finishing column is recycled to the reaction zone.

10. The method according to claim 1, wherein a portion of the light ends stream from the finishing column is recycled to the extraction column.

11. The method according to claim 1, wherein the reaction zone is operated at a temperature ranging from 60 to 150° C. and the acid catalyst comprises sulfuric acid in an amount ranging from 2 to 8 wt. % relative to the total weight of a bottoms stream exiting the reaction zone.

* * * * *